US011484407B2

(12) United States Patent
Wang et al.

(10) Patent No.: US 11,484,407 B2
(45) Date of Patent: Nov. 1, 2022

(54) TRANSCATHETER VALVE PROSTHESIS

(71) Applicant: HIGHLIFE SAS, Paris (FR)

(72) Inventors: Will Wang, Paris (FR); Malek Nasr, Paris (FR); Georg Börtlein, Paris (FR); Garrett Offerman, Paris (FR); Gilbert Madrid, Paris (FR); Martin Rothman, Paris (FR); Glenn Balke, Paris (FR); Eric Diep, Paris (FR)

(73) Assignee: HIGHLIFE SAS, Paris (FR)

( * ) Notice: Subject to any disclaimer, the term of this patent is extended or adjusted under 35 U.S.C. 154(b) by 163 days.

(21) Appl. No.: 16/736,116

(22) Filed: Jan. 7, 2020

(65) Prior Publication Data
US 2021/0205077 A1 Jul. 8, 2021

(51) Int. Cl.
*A61F 2/24* (2006.01)
(52) U.S. Cl.
CPC .......... *A61F 2/2418* (2013.01); *A61F 2/2409* (2013.01)
(58) Field of Classification Search
CPC ............................. A61F 2/2418; A61F 2/2409
See application file for complete search history.

(56) References Cited

U.S. PATENT DOCUMENTS

| 2012/0316642 | A1 | 12/2012 | Yu et al. | |
| 2018/0125649 | A1 | 5/2018 | Nasr | |
| 2018/0289474 | A1* | 10/2018 | Rajagopal | A61F 2/2418 |
| 2018/0296336 | A1* | 10/2018 | Cooper | A61F 2/2418 |
| 2018/0303612 | A1* | 10/2018 | Pasquino | A61F 2/2418 |

* cited by examiner

*Primary Examiner* — Suba Ganesan
(74) *Attorney, Agent, or Firm* — Oliff PLC

(57) ABSTRACT

A replacement heart valve system and a method of implanting a replacement heart valve in a patient. The replacement heart valve system includes a radially self-expandable tubular body and a valve including a plurality of leaflets coupled to the tubular body. The tubular body includes interconnected struts defining circumferential rows of cells, and has an outflow end and an inflow end that flares radially outward so as to have a larger outer diameter than that of the outflow end. A first row of proximal-most cells formed at the inflow end includes circumferentially adjacent cells that are disconnected from each other so as to be spaced from each other in the circumferential direction. A method of implanting the replacement heart valve includes delivering from a delivery catheter the tubular body, and expanding the tubular body such that the proximal-most cells are disposed against the native heart valve annulus.

16 Claims, 5 Drawing Sheets

TRANSCATHETER VALVE PROSTHESIS

BACKGROUND

Heart valve diseases affect approximately 300,000 people worldwide each year. Those diseases translate in abnormal leaflet tissue, for example, excess tissue growth, tissue degradation/rupture, or tissue hardening/calcifying. Those diseases may also translate in abnormal tissue position through the cardiac cycle of the heart, for example, annular dilation or ventricular reshaping. Such abnormal leaflet tissue and abnormal tissue position may lead to degradation in valve function including leakage/blood backflow (valve insufficiency) or a resistance to blood forward flow (valve stenosis).

A valve replacement procedure is a minimally invasive surgical procedure in which a patient's defective heart valve is repaired. Thus, the abnormal leaflet tissue or the abnormal tissue position may be repaired in order to restore operability of the heart valve. In a valve replacement procedure, a valve prosthesis is delivered to the patient's native heart valve without removing the patient's native heart valve. Instead, the valve prosthesis replaces the functions of the native heart valve.

SUMMARY

Disclosed herein are a replacement heart valve system and a method of implanting a replacement heart valve in a patient. The replacement heart valve system includes a radially self-expandable tubular body that includes a distal, outflow end, a proximal, inflow end that flares radially outward such that an outer diameter of the inflow end is larger than an outer diameter of the outflow end, and a plurality of interconnected struts that define circumferential rows of cells including a first row disposed at the inflow end. The first row is formed of proximal-most cells that form a proximal-most portion of the tubular body, are aligned in a circumferential direction, and include circumferentially adjacent cells that are disconnected from each other so as to be spaced from each other in the circumferential direction. A valve including a plurality of valve leaflets is coupled to the tubular body.

A method of implanting a replacement heart valve in a patient includes delivering from a delivery catheter the radially self-expandable tubular body, and expanding the tubular body such that the proximal-most cells are disposed against an annulus of a native heart valve.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DETAILED DESCRIPTION OF EMBODIMENTS

The following detailed description refers to the accompanying drawings that show, by way of illustration, specific details in which the disclosed embodiments may be practiced. Other embodiments may be utilized and structural and logical changes may be made without departing from the scope of the present disclosure. The various embodiments are not necessarily mutually exclusive, as some aspects of embodiments can be combined with one or more aspects of other embodiments to form additional embodiments.

The disclosed embodiments are directed toward a transcatheter valve prosthesis 1 for functional replacement of a patient's native heart valve in a connection channel. The patient's native heart valve may be, for example, an atrio-ventricular heart valve, such as a mitral valve or a tricuspid valve. Transcatheter valve prosthesis 1 may serve as an artificial replacement valve for the patient's native valve.

The native atrio-ventricular heart valve (e.g., a mitral valve or a triscupid valve) to be replaced has the generally circumferential wall structure forming a connection channel (or through opening) between the atrial 140 and ventricular 130 chambers of the heart. It includes a circumferential valve annulus, valve leaflets 160 opening the connection channel/through opening and closing the connection channel through opening at a position close to the valve annulus, a generally circumferential chord structure (chordae tendinae) 170 connected between the valve leaflets 160 and generally circumferential papillary muscle(s), and said circumferential papillary muscle(s).

Figure 1:
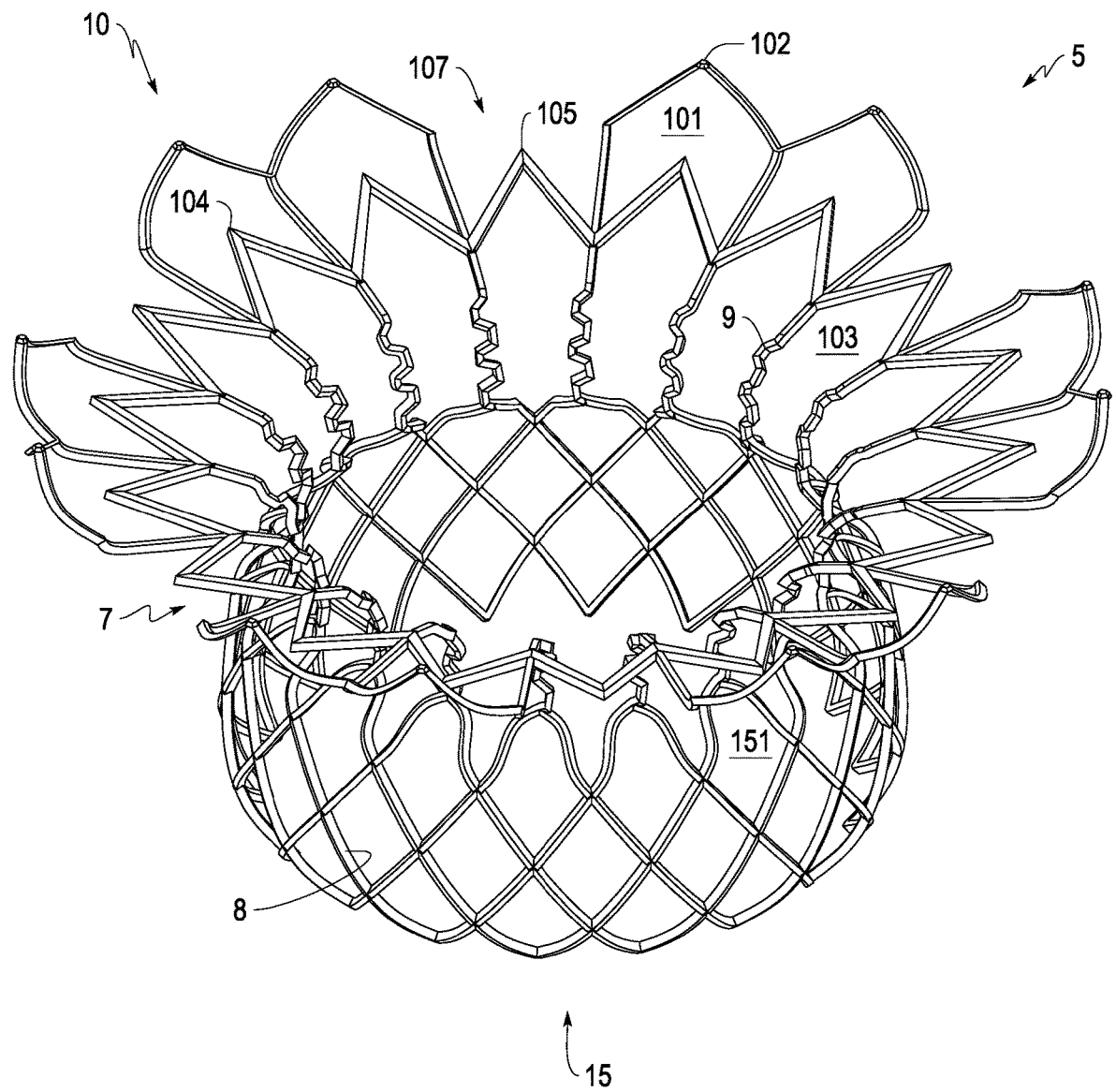
FIG. 1 schematically shows a transcatheter valve prosthesis according to the disclosed embodiments.
Figure 2:
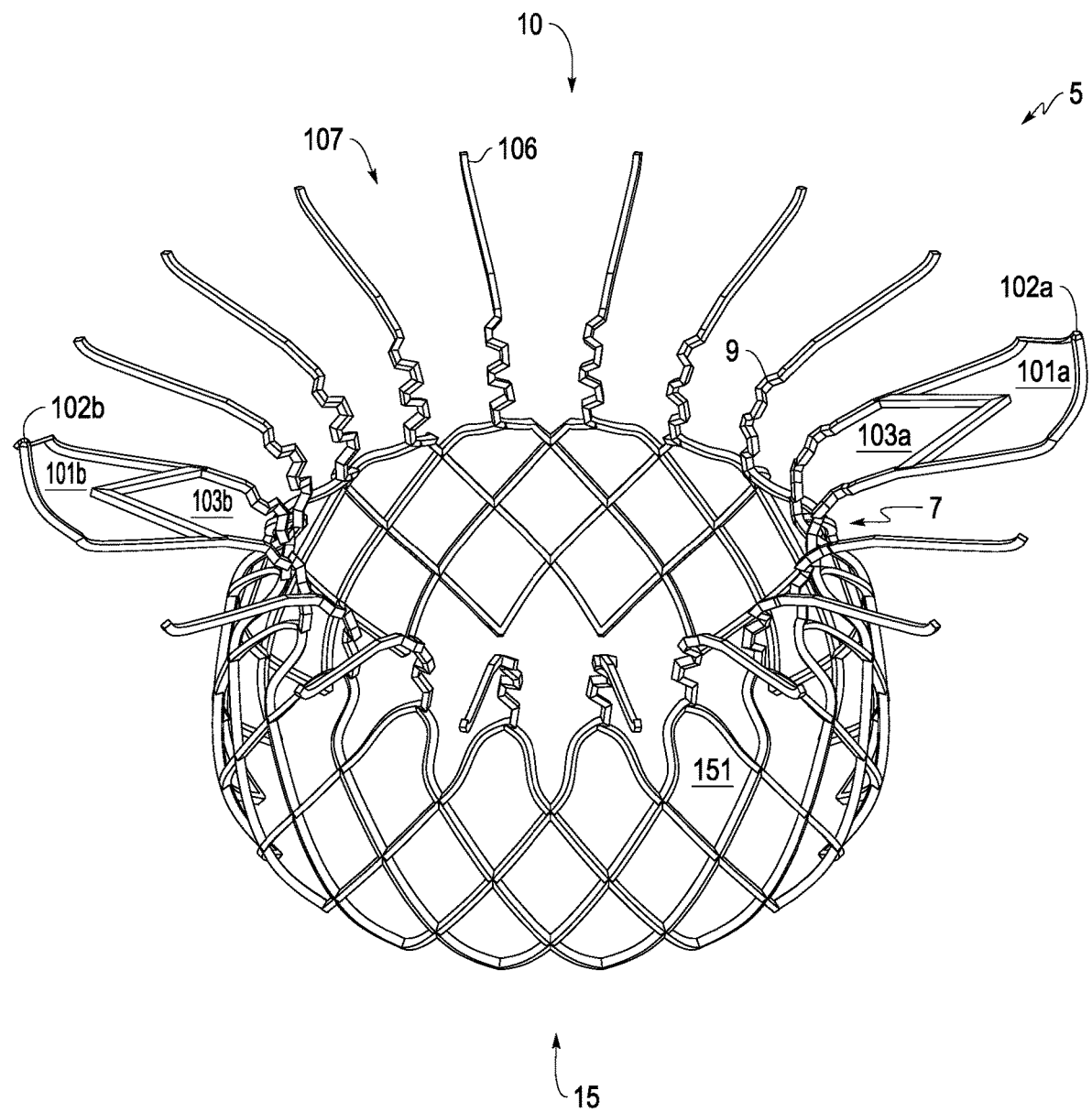
FIG. 2 schematically shows a transcatheter valve prosthesis according to the disclosed embodiments.

As shown in FIGS. 1 and 2, the transcatheter valve prosthesis 1 includes a radially, self-expandable tubular body 5 having a proximal, inflow end 10 and a distal, outflow end 15 (according to the direction of blood flow when the system is implanted in a patient) extending along a longitudinal axis. As used herein, "proximal" refers to a direction toward the inflow end 10, and "distal" refers to a direction toward the outflow end 15. In some embodiments, the tubular body 5 may be balloon expandable. The tubular body 5 may be formed of a mesh-like structure, which is delivered within a patient via a delivery catheter. The mesh-like structure of the tubular body 5 may include a plurality of struts 8 formed of a superalloy and/or a shape memory alloy including nickel, titanium, and/or precious metals (e.g., gold). In some embodiments, the tubular body 5 is formed of Nitinol. In other embodiments, tubular body 5 is formed of polymers including polyvinyl-chloride, polystyrene, polypropylene, and/or another polymer. For example, the tubular body 5 may be formed of one or more bioabsorbable polymers.

The tubular body 5 may be generally cylindrical in shape. The inflow end 10 of the tubular body 5 may flare radially outward so as to have a larger outer diameter than the outflow end 15. As discussed below, the tubular body 5 may further comprise a groove 7 that extends in a circumferential direction and is disposed between the inflow end 10 and the outflow end 15.

The inflow end 10 may have a generally conical or expanding shape along a central (longitudinal) axis of the tubular body, with its cross-section diameter increasing from the groove 7. The outflow end 15 may be generally cylindrical. Alternatively, both of the inflow end 10 and the outflow end 15 may have a conical shape along the axis of the tubular body, with their respective cross-sectional diameters increasing from the groove 7. Additionally, the outflow end 15 of the tubular body 5 may include a frustoconical shape that slopes radially outward from the preformed groove 7 toward the outflow (distal-most) end.

Figure 3:
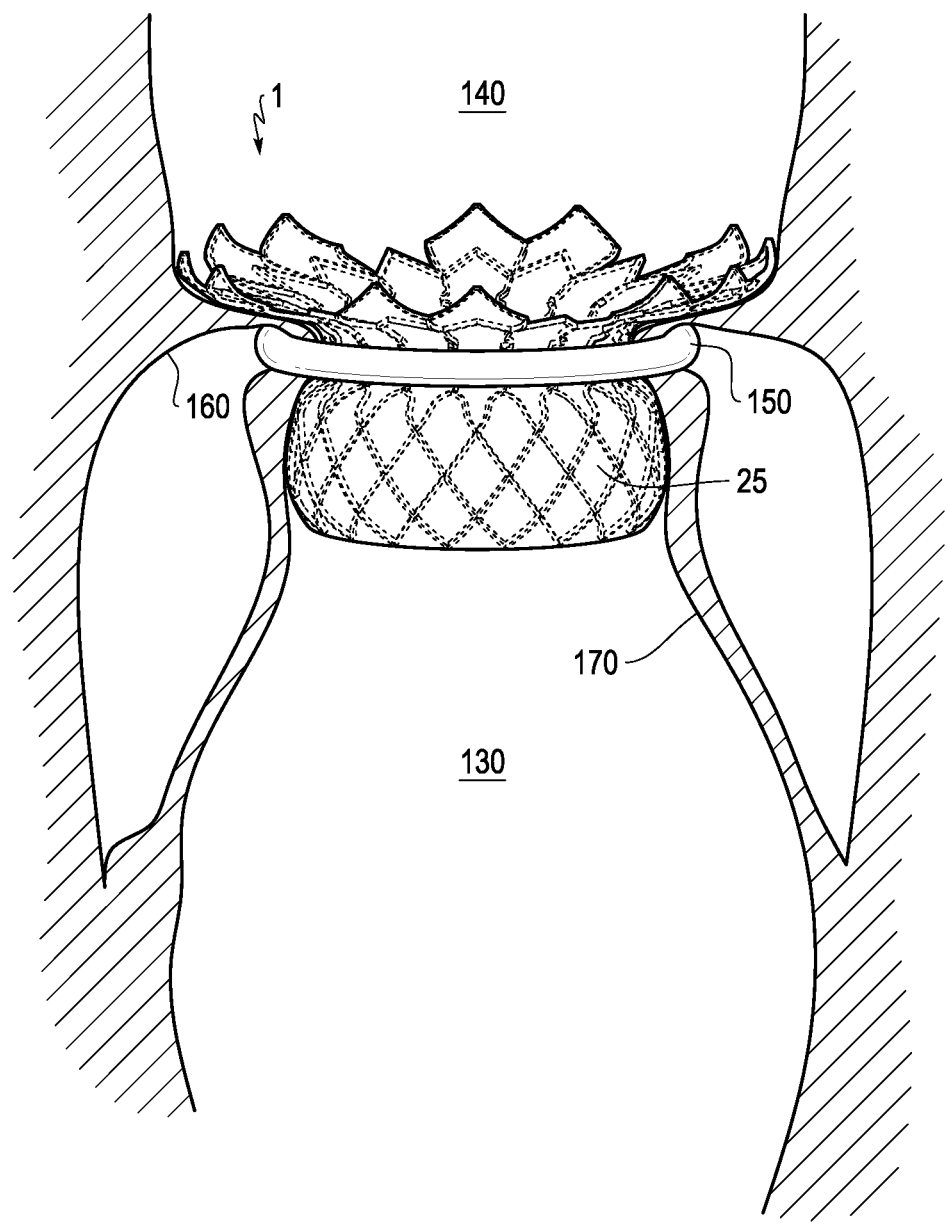
FIG. 3 schematically shows a transcatheter valve prosthesis implanted in a patient according to embodiments.
Figure 4:
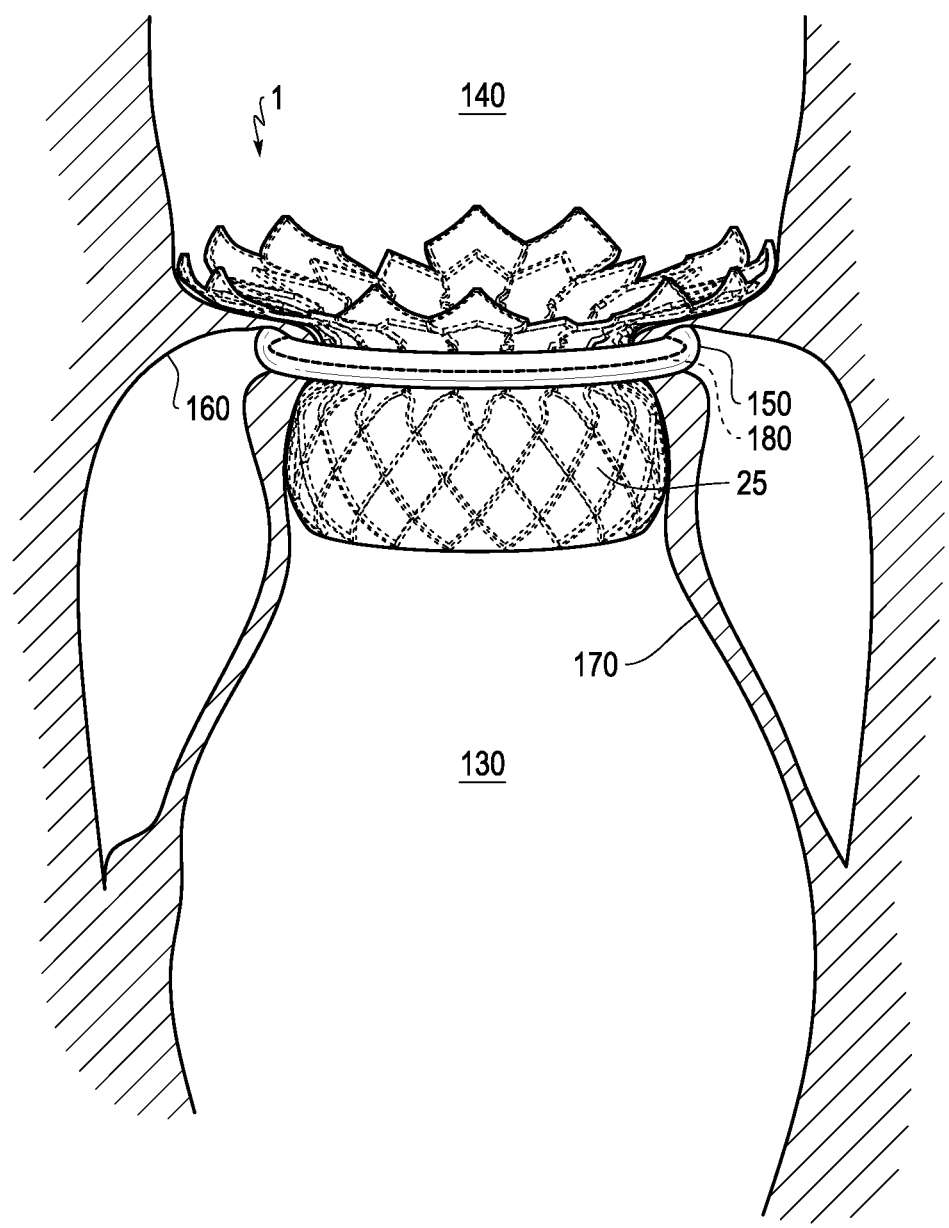
FIG. 4 schematically shows a transcatheter valve prosthesis implanted in a patient according to embodiments.

The outer diameter of the inflow end 10 may increase along a direction from the groove 7 to the proximal-most or inflow-most end portion 102. The inflow end 10 may be designed to be large enough to provide an effective paravalvular leakage seal. For example, as shown in FIGS. 3 and 4, the inflow end 10 is designed to be disposed against a surface of a native annulus when implanted into a patient. The inflow end 10 may be designed to be disposed against a surface of the native annulus in the left atrium 140 of the heart. The outflow end 15 of the tubular body 5 may include a frustoconical shape that slopes radially outward. Alternatively, outflow end 15 of tubular body 5 may be tapered inward.

The cross sections of the portions of the inflow end 10 and outflow end 15 may be or contain non-circular shapes such as elliptical or D-shaped cross sections. In addition, the direction of curvature in the axial profile (seen in an axial section along the tubular body 5) between the groove 7 and the inflow end 10 and/or between the groove 7 and outflow end 15 may change (e.g., from concave curvature of the groove 7 to a convex curvature at the transition between groove 7 and the inflow end 10 or outflow end 15).

Figure 5:
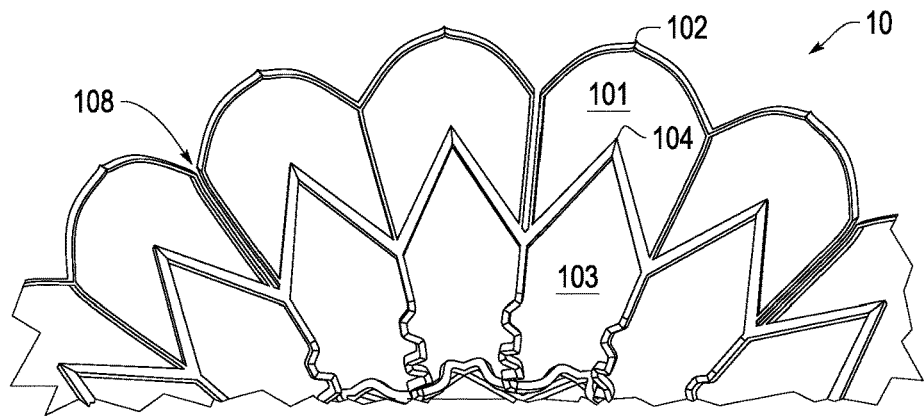
FIG. 5 schematically shows an inflow end of a transcatheter valve prosthesis according to embodiments.

The tubular body 5 includes a plurality of interconnected struts 8 that define circumferential rows of cells. The circumferential rows of cells include a first row 101 disposed at the inflow end 10. The first row is formed of proximal-most or inflow-most cells 101 that form a proximal-most or inflow-most portion of the tubular body. As shown in FIGS. 1, 2, and 5, the proximal-most cells 101 are aligned in a circumferential direction. For example, the apexes 102 of the proximal-most cells 101 are circumferentially aligned with each other. The proximal-most cells 101 include circumferentially adjacent cells that are disconnected from one another. That is, the proximal-most cells 101 include circumferentially adjacent cells that do not touch or are not directly joined or connected with one another. Rather, some of the cells 101 are spaced apart or separated from each other in the circumferential direction by one or more spaces 107 (FIGS. 1, 2, and 6B) or spaces 108 (FIGS. 5 and 6A) in the circumferential direction.

For example, in FIGS. 1 and 2, the first row includes disconnected cells 101 in which various struts have been eliminated, thereby forming an irregular circumferential inflow edge in which some cells 101 are spaced by spaces 107 from each other. In FIG. 5, the first row similarly includes disconnected cells 101 spaced from each other by spaces 108. Spaces 107 may be larger than spaces 108 in the circumferential direction. For instance, spaces 107 may have a circumferential dimension substantially equal to the circumferential dimension of a cell 101. Disconnected cells 101 may be spaced from each by one or more spaces 107, as shown in FIGS. 1 and 2. Spaces 108, shown in FIG. 5, may have a circumferential dimension substantially equal to a circumferential dimension of a strut.

The disclosed arrangements of the inflow end of the tubular body 5 provide non-uniform stent stiffness to the tubular body 5. For example, the disclosed non-uniform stent stiffness arrangements of the tubular body 5 enable greater stent conformity to patient anatomy to be achieved while maintaining the desired stent structural integrity and function. Non-uniform stent stiffness can be achieved by selectively creating strut interruptions and varying strut connections, as shown in FIGS. 1, 2, and 5-6B. For example, by designing the inflow end 10 to include a row of proximal-most cells 101 that are aligned in the circumferential direction and include circumferentially adjacent cells that are disconnected from one another so as to not touch one another or be separated from each other by a space in the circumferential direction, non-uniform stent stiffness around the circumference and/or along the length of the tubular body 5 can be achieved.

As a result of the claimed configurations, in-folding or stent invagination may be eliminated. In-folding or stent invagination is when some of the inflow end cells buckle inwards, thereby creating center-pointed stent invagination. Stent invagination or in-folding may occur under various circumstances, including, for example, when a valve prosthesis is implanted in a native valve having a smaller geometry than the valve prosthesis. By designing the inflow end 10 of the tubular body 5 to have proximal-most cells 101 that are disconnected from each other (e.g., not in touching contact with each other or spaced from one another by one or more spaces 107 or 108), the inflow end 10 of the tubular body 5 can be more easily distribute stress in small native or tight native valves and thus avoid strut buckling or in-folding. The more flexible inflow end of the tubular body 5 makes the prosthesis 1 more adaptable to different patient anatomies, while still remaining functional and durable. Additionally, the disconnected cells 101 enable easier valve loading and a smaller delivery profile, and functional evaluation of the prosthetic valve can be better evaluated without fully deploying the valve from the delivery system.

As shown in FIG. 1, the proximal-most cells 101 of the first row may include a plurality of pairs of touching cells directly joined with each other. The plurality of pairs of cells 101 are spaced from circumferentially adjacent pairs by space 107. The pairs of cells 101 may be disposed at equal distances from one another around a circumference of the inflow end 10 of the tubular body 5, as shown in FIG. 1, or may be disposed at non-equal distances from each other in the circumferential direction. The tubular body 5 is not limited to the configuration shown in FIG. 1 (or the configurations shown in FIGS. 2-6B discussed below). Other configurations of the proximal-most cells 101 of the first row are possible so long as at least some of the cells 101 are disconnected from each other such that they are separated or spaced from one another in a circumferential direction (e.g., at least some cells 101 do not touch each other in the circumferential direction absent force, such as a radial inward force).

For example, the proximal-most cells 101 of the first row may include a single pair of touching cells 101 directly joined with each other, with the other cells 101 of the first row being disconnected from each other such that they are not in touching contact with each other or are spaced from each other by spaces 107. The proximal-most cells 101 of the first row may include two pairs of touching cells 101 disposed on radially opposite sides of the tubular body 5. In yet another embodiment, the proximal-most cells 101 may include more than two pairs of touching cells 101 directly joined with each other. The pairs of touching cells 101 may be disposed at equal or non-equal distances from one another in the circumferential direction. The proximal-most cells 101 may include more than two touching cells 101 directly joined with each other so long as the group of touching cells 101 is disconnected from (e.g., does not touch) at least one circumferentially adjacent cell. For example, the proximal-most cells 101 may include one or more groups of 2, 3, 4, 5, or more cells directly joined with each other so long as the group(s) are disconnected from at least one circumferentially adjacent cell. The groups of directly joined cells 101 may include different numbers of cells 101. For example, the first row may include a first group of 2, 3, 4, 5, 6, or more cells 101 spaced from a second group of a different number of directly joined cells 101. The groups and/or individual cells may be spaced from one another by one or more spaces 107 in the circumferential direction. The cells 101 and/or groups of joined cells 101 may be equally or non-equally spaced from circumferentially adjacent cells or groups of cells 101 around the circumference of the inflow end 10 of the tubular body 5. An apex 105 of a cell 103 of a second row may be disposed between circumferentially adjacent pairs of touching cells 101 or individual cells 101 so as to axially overlap space 107.

Alternatively, the first row may include no touching or directly joined cells 101. For example, the first row may include only individual cells 101 that are disconnected (e.g., spaced) from each other such that the cells 101 are not in touching contact with any of the other proximal-most cells 101. Rather, each cell 101 is spaced from a circumferentially adjacent cell 101 by space 107. The individual cells 101 may be disposed at equal or non-equal distances from one another in the circumferential direction. Any suitable number of individual cells 101 may form the first row. For example, the first row could include only one proximal-most cell 101, or the first row could include 2, 3, 4, 5, 6, 7, 8, 9, 10, or more proximal-most cells that are circumferentially spaced from one another by spaces 107. The cells 101 may be disposed at non-equal distances from one another. The cells 101 may be designed to have any suitable shape, and may be formed to have an apex 102 as the proximal-most point of the tubular body 5.

In FIG. 1, the cells 101 may be designed to have any suitable shape, and may be formed to have apexes 102 as the proximal-most points of the tubular body 5. The apexes 102 may be circumferentially aligned with each other. As discussed in more detail below, cells 103 of a second row of cells may have a proximal-most portion 105 that extends toward the inflow side so as to be disposed at a position between disconnected cells 101 in the circumferential direction. For example, a proximal-most portion 105 of cells 103 may overlap a space 107 in the axial direction. The proximal-most portions 105 of cells 103 may form apexes like proximal-most portions 102 of cells 101. The proximal-most apexes 102 of cells 101 may be positioned proximally of the proximal-most portions 105 of the cells 103 of the second row. Additionally, the proximal-most apexes 102 of cells 101 and the proximal most portions 105 of cells 103 may together define the inflow-most end of the tubular body 5. Cells 103 that are aligned with cells 101 in the axial direction may also include proximal-most portions 104. Struts forming proximal-most portions 104 may also define a distal-most end of cells 101.

Alternatively, the first row could include two proximal-most cells 101*a*, 101*b*, as shown in FIG. 2. The cells 101*a*, 101*b* in FIG. 2 are disposed at radially opposite sides of the tubular body 5. Alternatively, cells 101*a*, 101*b*, may be disposed at different positions around the circumference of the inflow end 10 of the tubular body 5. Additionally, the proximal-most or inflow-most cells 101 of the first row may include more or fewer cells than cells 101*a*, 101*b* in FIG. 2. The proximal-most cells 101*a*, 101*b* may be disposed at equal (see FIG. 2) or non-equal distances from each other around the circumference of the inflow end. As discussed above with respect to FIG. 1, the proximal-most cells 101 may include one or more pairs (having two) or groups (having more than two) of touching cells directly joined with each other so long as the one or more pairs or groups of touching cells are disconnected from (e.g., do not touch) at least one circumferentially adjacent cell in the first row. Alternatively, the first row may include no touching cells 101. For example, the first row may include only individual cells 101 that are disconnected (e.g., spaced) from each other such that the cells 101 are not in touching contact with any of the other proximal-most cells 101. The individual cells 101 may be disposed at equal or non-equal distances from one another in the circumferential direction. As discussed above with respect to FIG. 1, any suitable number of individual cells 101 may form the first row.

In FIG. 2, the cells 101*a*, 101*b* that are disposed on radially opposite sides of the tubular body 5 may be designed to have any suitable shape, and may be formed to have apexes 102*a*, 102*b* as the proximal-most points of the tubular body 5. The apexes 102*a*, 102*b* may be circumferentially aligned with each other. The cells 101*a*, 101*b* are not in touching contact with each, nor are they directly joined to each other. Instead, cells 101*a*, 101*b* are spaced from each other by one or more spaces 107 in the circumferential direction. As discussed in more detail below, a plurality of arms 106 that extend from a distal row of cells 106 extend toward the inflow side such that a portion of each of the arms 106 is disposed at a position between the cells 101*a*, 101*b* in the circumferential direction. For example, the arms 106 may define spaces 107. The proximal-most apexes 102*a*, 102*b* may be positioned proximally of a proximal-most portion of the arms 106 positioned between the proximal-most cells 101*a*, 101*b* in the circumferential direction.

As shown in FIG. 5, the proximal-most cells 101 may include a plurality of pairs of touching cells directly joined with each other that are spaced from circumferentially adjacent pairs by space 108. Alternatively, each cell 101 in the first row may be spaced from circumferentially adjacent cells by space 108. That is, the first row or inflow-most row of cells 101 may include no cells that are directly joined or connected to each other in the circumferential direction. Rather, the inflow-most row of cells 101 may include only individual cells 101 that are spaced from each other by spaces 108.

Alternatively, individual cells 101 or groups of 2, 3, 4, 5, 6, 7, 8, or more cells 101 that are directly joined to each other in the circumferential cells may be spaced in the circumferential direction from circumferentially adjacent cells by a space 108. For example, the proximal-most cells 101 may include one or more groups of 2, 3, 4, 5, or more cells directly joined with each other so long as the group(s) are disconnected from at least one circumferentially adjacent cell. The disconnected cells 101 may be disposed at equal or non-equal distances from one another in the circumferential direction. For instance, an individual cell 101 may be spaced by space 108 from a group of 2 or more cells that are directly joined to each other, or a first group of cells 101 may be spaced from a second, circumferentially adjacent group of cells 101 such that the first group has more cells than the second group. In other words, the inflow end 10 may include different numbers of directly joined cells 101. Put yet another way, spaces 108 may be positioned as equal or non-equal distances from one another in a circumferential direction around the inflow end 10 of the tubular body 5.

The cells 101 of FIG. 5 may be designed to have any suitable shape, and may be formed to have apexes 102 as the proximal-most point of the tubular body 5. The apexes 102 may be circumferentially aligned with each other. As discussed in more detail below, cells 103 of a second row of cells may have proximal-most portions 104. Proximal-most portions 104 may form apexes, as shown in FIG. 5. Proximal-most portions 104 of cells 103 of the second row may also define a distal-most portion of cells 101 of the first row.

As discussed above, space 108 may be smaller than space 107. Space 108 may have a smaller circumferential dimension than that of space 107. For example, space 108 may have a circumferential dimension substantially equivalent to that of a strut forming the inflow end 10 of the tubular body 5. In the arrangement of the inflow end 10 shown in FIG. 5, disconnected cells 101 may overlap each other in the circumferential direction under radial compression so as to adapt the inflow end 10 conform to the native anatomy without buckling or in-folding. For example, under radial compression from the native valve annulus, disconnected cells 101 may be compressed so as to overlap one another in the circumferential direction. The disconnected cells 101 may be radially compressed so as to overlap each in a fan-like manner. Such flexibility enables the tubular body 5 to better conform to the native valve anatomy, thereby preventing or reducing paravalvular leakage.

The inflow end 10 of the tubular body 5 may include a combination of spaces 107 and 108. For example, individual or groups of cells 101 may be separated from circumferentially adjacent cells by a combination of spaces 107 and spaces 108. Various other modifications and combinations of elements between FIGS. 1, 2, and 5 are readily permissible so long as the first row of proximal-most cells 101 includes circumferentially adjacent cells that are separated from one another by a space 107 and/or 108 in the circumferential direction (e.g., are not in touching contact or are not directly joined to one another).

As a result of the configuration of the proximal-most portion, the first row 101 may include fewer cells than a remainder of circumferential rows of the tubular body 5 (see FIGS. 1 and 2). As shown in FIGS. 1, 2, and 5, the proximal-most cells 101 may each include a proximal-most apex 102 positioned proximally of a proximal-most portion 105 of struts positioned between the proximal-most cells 101 in the circumferential direction.

As shown in FIGS. 1, 2, and 5, the tubular body 5 may further include a second row of cells 103 axially adjacent to the first row of cells 101. The first row 101 may include fewer cells than the second row of cells 103, as shown in FIGS. 1 and 2, or the first row of cells 101 and the second row of cells 103 may include an equal number of cells, as shown in FIG. 5. The cells 103 of the second row may be larger than the proximal-most cells 101 of the first row. The cells 103 of the second row may be larger than any of the other cells in the tubular body 5.

A proximal portion 105 of a cell 103 of the second row may be disposed at a position between the circumferentially adjacent cells 101 that do not touch, as shown in FIG. 1. For example, a proximal portion 105 of a cell 103 of the second row may be disposed so as to overlap space 107 in the axial direction. That is, a proximal portion 105 may be circumferentially aligned with space 107. The proximal portion 105 of the cell 103 of the second row may form an apex between disconnected cells 101. The second row of cells 103 may not include any spaces, such as spaces 107 or 108. That is, all of the cells 103 of the second row may be directly joined to circumferentially adjacent cells, as shown in FIGS. 1 and 5. Alternatively, the second row of cells 103 may include spaces 107 defined by arms 106, as shown in FIG. 2.

A distal portion (e.g., outflow portion) 104 of each of the proximal-most cells 101 may be defined by struts that also define a portion of an axially adjacent cell 103 of the second row, as shown in FIGS. 1, 2, and 5. The distal portion 104 of each of the proximal-most cells 101 may be defined by struts that also define an apex of an axially adjacent cell 103 of the second row. The apexes 102, 104, 105 may have a "V"-shape or a "U"-shape, or any other suitable shape. The apexes or peaks 102, 104, 105 may be oriented so point in the proximal direction (e.g., in the inflow direction).

As shown in FIG. 2, the tubular body 5 may include a second row of cells 103a, 103b axially adjacent to the first row of cells 101a, 101b. The first row 101 may include fewer cells than the second row of cells 103. The cells 103a, 103b of the second row may be larger than the proximal-most cells 101a, 101b of the first row. The cells 103a, 103b of the second row may be larger than any of the other cells in the tubular body 5. Instead of the proximal portion 105 being positioned between the non-touching cells 101a, 101b, a plurality of arms 106 is disposed between the cells 101a, 101b in the circumferential direction. The arms 106 may extend from an apex or peak of the cells 151 of the distal row, as shown in FIG. 2.

Although FIG. 2 shows a plurality of arms 106 disposed between the cells 101a, 101b, the tubular body 5 may include any suitable number of arms 106 between the cells 101a, 101b, such as one or more arms 106. Alternatively, the tubular body 5 may include a combination of proximal apex portions 105 (see FIG. 1) and arms 106 (see FIG. 2) between non-touching cells 101 of the first row. The arms 106 shown in FIG. 2 may be used in combination with pairs (having two) or groups (having more than two) of touching or joined cells 101, as shown in FIG. 1. Similarly, the proximal portions 105 of the cells 103 of the second row shown in FIG. 1 may be disposed in between individual disconnected cells 101a, 101b shown in FIG. 2. Various other modifications and combinations of elements between FIGS. 1, 2, and 5 are readily permissible so long as the first row of proximal-most cells 101 includes circumferentially adjacent cells that are separated from one another by a space 107 and/or 108 in the circumferential direction (e.g., are not in touching contact or are not directly joined to one another).

As shown in FIGS. 1 and 2, the tubular body 5 may include a distal row of cells 151 disposed closer to the outflow end 15 than the first row of proximal-most cells 101. The distal row of cells 151 may be positioned on a distal side of the groove 7 so as to be closer to the outflow end 15 than the groove 7. As shown in FIG. 2, the tubular body 5 may include an arm 106 that extends from the distal row of cells 151 such that a portion of the arm 106 is disposed between the circumferentially adjacent cells 101a, 101b that do not touch. The arm 106 may extend from an apex of a cell of the distal row 151. Although FIGS. 5, 6A, and 6B only show the inflow end 10 of the tubular body 5, they may have the same features of tubular body 5 shown in FIGS. 1-4 and discussed herein.

The tubular body 5 is not limited to the configuration shown in FIGS. 1, 2, and 5. Other configurations of the proximal-most cells 101 of the first row are possible so long as at least some of the cells 101 are disconnected from each other such that they are separated from each other in the circumferential direction by one or more spaces 107 and/or 108.

Figure 6A:
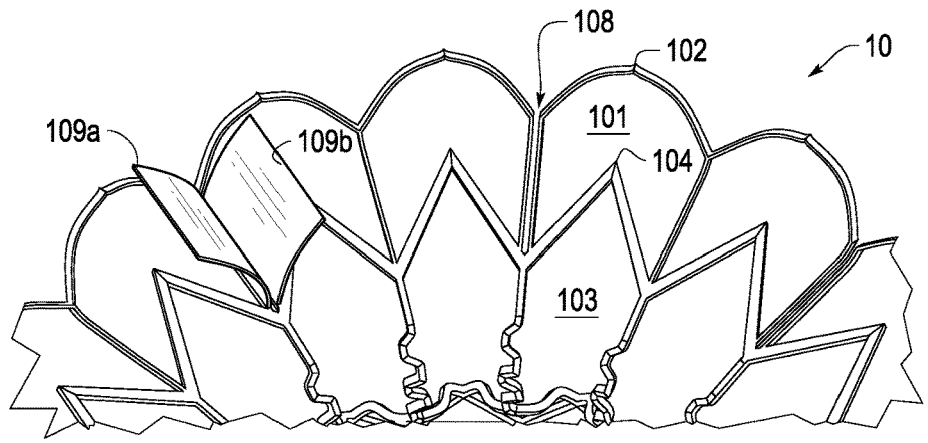
FIGS. 6A and 6B shows inflow ends of transcatheter valve prosthesis according to embodiments.
Figure 6B:
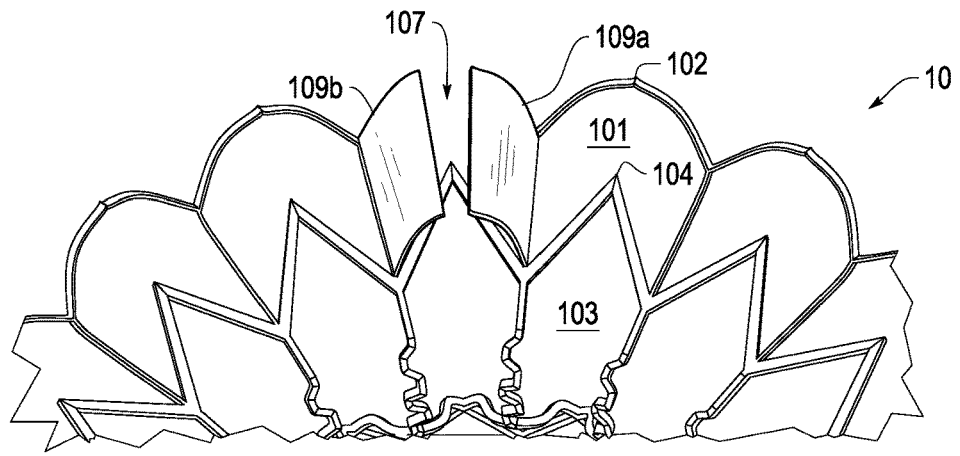

As shown in FIGS. 6A and 6B, the circumferentially disconnected cells 101 of the proximal-most or first row may include seals 109. A seal 109 may be attached to a side of a cell 101 bordering space 107 or 108 so as to extend in the circumferential direction toward a circumferentially adjacent cell 101 (e.g., that also borders space 107 or 108. Both disconnected cells 101 have sides forming space 107 or 108 may include a seal 109. For example, as shown in FIGS. 6A and 6B, disconnected cells 101 having sides forming a space 107 or 108 may respectively have a seal 109a and 109b. The seals 109a and 109b may extend from the side of a respective cell 101 toward the other cells 101 in the circumferential direction so as to overlap each other in the circumferential direction and seal the spaces 107, 108. Alternatively, only one of the disconnected cells 101 may include a seal 109. Each space 107 and/or 108 may be partially or completely covered by at least one seal 109, or only some spaces 107 and/or 108 may be covered by one or more seals 109, as shown in FIGS. 6A and 6B.

The seals 109 may be formed of struts or a wire extension covered with fabric or any other suitable material. For example, any fabric or material discussed below may be used. The seals 109 may have any suitable shape or size. For example, although the seals 109 shown in FIGS. 6A and 6B have a rectangular shape, the seals 109 may be in the shape of a half or semi-circle, square, triangle, diamond, star, pentagon, trapezoid, hexagon, polygon, parallelogram, heptagon, octagon, nonagon, or any other suitable shape. The seals 109 may extend to a circumferentially adjacent cell 101 across space 107 or 108 or may extend partially across space 107. The seals 109 may both extend on a radially inner side of the tubular body 5, as shown in FIGS. 6A and 6B, or the seals 109 may extend on a radially outer side of the tubular body 5. Alternatively, one seal may extend on a radially outer side and another seal may extend on a radially inner side of the tubular body 5. The seals 109 may help seal the prosthetic valve to the native valve annulus (e.g., to form a blood tight seal therebetween), to prevent undesirable paravalvular leakage and/or regurgitation at the implantation site.

Adjacent seals 109a, 109b may extend towards each other in the circumferential direction so as to radially overlap each other in order to facilitate sealing of the tubular body 5 to the native valve annulus. Adjacent seals 109a, 109b may radially overlap each other on a radially inner side of the tubular body 5 or may radially overlap each other on a radially outer side of the tubular body 5. Alternatively, one of the seals 109a, 109b may be extend on a radially inner side and the other seal 109a, 109b may extend on a radially outer side such that the seals radially overlap each other on opposite radial sides of the tubular body 5. Alternatively, adjacent seals 109a, 109b may not overlap each other. For example, adjacent seals 109a, 109b may extend towards each other in opposite circumferential directions so as to not overlap such that the seals 109a, 109b only partially cover space 107, 108. Alternatively, adjacent edges or sides of the seals 109a, 109b may be in touching contact without overlapping each other in the radial direction.

As shown in FIGS. 1 and 2, the tubular body 5 may also include flexible struts 9. Such flexible struts 9 may have an S-shape. The S-shaped struts 9 may overlap the groove 7 or may be disposed on an inflow (e.g., proximal) side of the groove 7. The S-shaped struts 9 may form part of arms 106 (see FIG. 2) or a side of the cells 103 of the second row (see FIG. 1). The S-shaped struts 9 may each form a decorrelation portion that dissociates movements between inflow end 10 of the tubular body 5 and the outflow end 15 of the tubular body 5. Thus, the S-shaped struts 9 may be configured to stress and compress in reaction to movement of the inflow end 10 or the outflow end 15. Thus, because the S-shaped struts 9 stretch and/or compress movement from one end of the tubular body 5 does not translate/communicate to the other end of the tubular body 5. The S-shaped struts 9 may be disposed entirely proximal of preformed groove 7 in an inflow direction.

The groove 7 of the tubular body 5 may be open to the radial outside of the tubular body 5. The preformed groove 7 may be an indentation in the mesh-like structure of tubular body 5 that defines a channel. As shown in FIGS. 1 and 2, the preformed groove 7 may extend around an entire outer circumference of tubular body 5. In other embodiments, the preformed groove 7 may extend less than the entire outer circumference of tubular body 5. The preformed groove 7 may be a continuous, non-interrupted groove, or may be an interrupted groove having, for example, two or more groove portions. In some embodiments, the preformed groove 7 may be located at an axial distance, along the longitudinal axis of the tubular body 5, from both the inflow end 10 and the outflow end 15 of the tubular body 5. Thus, the preformed groove 7 may be axially spaced apart from proximal-most and distal-most ends of the tubular body 5.

The preformed groove 7 may be delimited by projections (not shown) that protrude outward from the tubular body 5. Thus, in some embodiments, the tubular body 5 may include a first set of projections that are disposed above the preformed groove 7, in an inflow direction, and a second set of projections that are disposed below the preformed groove 7, in an outflow direction. Thus, the first and second set of projections may surround a top and bottom portion of the preformed groove 7. The first and second set of projections may be directed toward each other. Additionally, the first and second set of projections may be members configured to pierce tissue such as, for example, spikes, triangular projections, barbs, etc.

As shown in FIGS. 3 and 4, a tubular fabric 25 may be disposed on an outer surface of the tubular body 5. The fabric 25 may cover an entire outer surface of the tubular body 5, or only a portion of the outer surface of the tubular body 5. The fabric 25 may be disposed within the groove 7 such that the fabric 25 follows the contours of the groove 7. The fabric 25 may be slack or tightly disposed on the tubular body 5. As discussed further below, a trapping member 150 may be disposed around tubular body 5. The fabric 25 may be disposed on the tubular body 25 such that it is in a slack state until the trapping member 150 is disposed around the tubular body 25. Thus, the trapping member 150 may cause the fabric 25 to be moved into preformed groove such that the fabric 25 is in a tensioned state.

The fabric 25 may be formed of a polymer material including, for example, polyester fabric (e.g., DACRON® or other PTFE graft material). Additionally or alternatively, the fabric 25 may formed of pericardium and/or a metal mesh material (e.g., a metal mesh formed of Nitinol). In some embodiments, the fabric 25 may include one or more segments of material. For example, the fabric 25 may include two, four, or six segments of material. The segments may be spaced apart, providing gaps between adjacent segments. Alternatively or in addition, some or all adjacent segments may overlap. The fabric 25 may include one layer of material or multiple layers of materials. In some embodiments, the fabric 25 may include a coating or a liner.

The fabric 25 may be attached to tubular body 5 through any known securing mechanism. For example, the fabric 25 and the tubular body 5 may be secured through an adhesive and/or sutures. The fabric 25 may be configured to assume a deployed, expanded configuration and a contracted, reduced configuration with the tubular body 5. Thus, the fabric 25 may be expanded and contracted based on the state of the tubular body 5.

The tubular body 5 may be coupled to an artificial heart valve (not shown) such that the valve is arranged within the tubular body 5. The valve may include a plurality of valve leaflets. The valve may serve as an artificial replacement for a patient's native heart valve (for example, a mitral and/or a tricuspid valve). For example, the valve can be arranged on a radially inner side tubular body 5 so as to be coupled to a radially inner side of one or more struts 8. The valve may be coupled to a radially inner side of the tubular body 5 at a position proximate to the groove 7 or may be coupled to an outflow end 15 of the tubular body 5 such that the valve leaflets extend in a distal direction from the outflow end 15 of the tubular body 5.

All embodiments of valve prosthesis 1 may include positioning and/or orientation devices (not shown) to facilitate relative and/or absolute positioning of the tubular body 5. These devices may include passive markers that are fixedly attached to the tubular body 5. The passive markers may be made from materials different from the materials of the tubular body 5 in order to improve contrast during medical imaging, e.g., using magnetic resonance or X-ray based imaging techniques. The passive markers may, for example, be made of highly radio-opaque materials thereby allowing one to precisely acquire the relative and/or absolute position of the components of valve prosthesis 1 with respect to the patient's body.

FIGS. 3 and 4 show the valve prosthesis 1 implanted in a native valve (e.g., mitral valve) of a patient. The valve prosthesis 1 may be deployed, via a catheter, to a patient. The method of delivering valve prosthesis 1 may include delivering, from a delivery catheter, the tubular body 5 in which a valve is disposed.

Next, as shown in FIGS. 3 and 4, the tubular body 5 and valve may be expanded such that the proximal-most cells 101, 101*a*, 101*b* are disposed against the annulus of the native valve. For example, the proximal-most cells 101, 101*a*, 101*b* may be disposed in the atrium 140 (e.g., left atrium) so as to be disposed against an atrial surface of the annulus of the native valve. The tubular body 5 may be expanded such that the second row of cells 103 is also disposed against the annulus of the native heart valve, for example, the atrial 140 surface of the annulus of the native valve. Additionally or alternatively, the tubular body 5 may be expanded such that the arms 106 are also disposed against the annulus of the native heart valve, for example, the atrial 140 surface of the annulus of the native valve.

Thus, for example, valve prosthesis 1 may be delivered to a patient's defective mitral or tricuspid valve in order to restore operability. Valve prosthesis 1 may be delivered to a patient so that the preformed groove 7 is located on the ventricular 130 side of the annulus of the native valve (e.g., having a distance from the native valve annulus).

To place valve prosthesis 1 within the patient's heart valve, the following approaches may be applied: (1) an arterial retrograde approach entering the heart cavity over the aorta, (2) through a venous access and through a puncture through the inter atrial septum (trans-septal approach), (3) over a puncture through the apex of the heart (trans-apical approach), (4) over a puncture through the atrial wall from outside the heart, (5) arterial access (e.g., from the femoral artery through a puncture in the groin), (6) directly through the vena cava and into the right atrium (for a tricuspid valve replacement, for example), or (7) any other approach known to a skilled person.

For functional replacement of a patient's heart valve, the valve prosthesis 1 may be fixed relative to the patient's connection channel wall structure such that an exterior of valve prosthesis 1 is sealed against blood flow. To achieve this, tissue of the patient's connection channel wall structure adjacent to the preformed groove 7 may be forced or placed inside preformed groove 7.

The method may further include advancing a trapping member 150 around the tubular body 5 and around the preformed groove 7. Thus, the trapping member 150 may trap portions of native valve leaflets 160 and/or chords 170 in preformed groove 7. This may help secure the tubular body 5 in a patient. The trapping member 150 may include a full or partial loop. Additionally, the trapping member 150 may be moved around the tubular body 5 after the tubular body 5 is fully expanded or when the tubular body 5 is only partially expanded. The trapping member 150 may be loosely disposed within the preformed groove 7 such that an interference fit between the trapping member 150 and the preformed groove 7 secures the tubular body 5 in place. Thus, the trapping member 150 may serve to anchor the valve prosthesis 1 within the patient. In other embodiments, the trapping member 150 may exert an inward, radial force on the tubular body 5 in order to anchor valve prosthesis 1 within the patient. Thus, in this embodiment, the trapping member 150 may exert a frictional force on the native valve leaflets 160 and/or chords 170.

The trapping member 150 may include a delivery configuration within a delivery catheter and a deployment configuration in which the trapping member 150 is deployed from the delivery catheter. In embodiments, the trapping member 150 may be biased to the deployment configuration. For example, the trapping member 150 may include a shape-memory alloy such as a Nitinol or a Nitinol-based alloy.

In some embodiments, an elongate outer member 180 (see FIG. 4) may also be advanced around the tubular body 5 and around the preformed groove 7. The elongate outer member 180 may encircle the tubular body 5 after the tubular body 5 is fully expanded or when the tubular body 5 is only partially expanded. The elongate outer member 180 may force the patient's native valve leaflets 160 and/or chords 170 in the preformed groove 7. The trapping member 150 may then be disposed over and along the elongate outer member 180 in order to advance the trapping member 150 around the tubular body 5 and into the preformed groove 7. The elongate outer member 180 may then be removed from the patient after the trapping member 150 is disposed around tubular body 5. After the elongate outer member 180 is removed from the patient, the trapping member 150 may maintain the patient's native valve leaflets 160 and/or chords 170 in preformed groove 7.

In some embodiments, the elongate outer member 180 may be a guidewire. The elongate outer member 180 may have a diameter smaller than a diameter of trapping member 150.

The disclosed methods of using valve prosthesis 1 may result in fixation of the tubular body 5 in the patient's connection channel wall structure with minimal occlusion of the patient's native valve.

What is claimed is:

1. A replacement heart valve system, comprising:
   a radially self-expandable tubular body comprising:
   a distal, outflow end,
   a proximal, inflow end that flares radially outward such that an outer diameter of the inflow end is larger than an outer diameter of the outflow end, and a plurality of interconnected struts that define circumferential rows of cells including:
  a first row disposed at the inflow end, the first row being formed of proximal-most cells that:
    form a proximal-most portion of the tubular body,
    are aligned in a circumferential direction, and
    include circumferentially adjacent cells that are disconnected from each other so as to be spaced from each other in the circumferential direction by a space, and
  a second row of cells adjacent to the first row of cells, a proximal portion of a cell of the second row being disposed in the space between two circumferentially adjacent cells of the first row so as to overlap the first row in the circumferential direction, and
a valve coupled to the tubular body, the valve including a plurality of valve leaflets,
wherein the cells of the second row are larger than the proximal-most cells of the first row.

2. The replacement heart valve system according to claim 1, wherein the proximal-most cells each include a proximal-most apex positioned proximally of a proximal-most portion of struts positioned between the proximal-most cells in the circumferential direction.

3. The replacement heart valve system according to claim 1, wherein circumferentially adjacent cells of the second row are joined to each other such that the second row does not include any spaces between circumferentially adjacent cells.

4. The replacement heart valve system according to claim 1, wherein a distal portion of each of the proximal-most cells is defined by struts that also define a portion of an axially adjacent cell of the second row.

5. The replacement heart valve system according to claim 1, wherein the proximal portion of the cell of the second row forms an apex between the circumferentially adjacent cells that are spaced from each other.

6. The replacement heart valve system according to claim 1, wherein a distal portion of each of the proximal-most cells is defined by struts that also define an apex of an axially adjacent cell of the second row.

7. The replacement heart valve system according to claim 1, wherein the tubular body further comprises a distal row of cells disposed closer to the outflow end than the first row of proximal-most cells, and an arm that extends from the distal row of cells such that a portion of the arm is disposed between the circumferentially adjacent cells that are spaced from each other.

8. The replacement heart valve system according to claim 7, wherein:
  the tubular body further comprises a groove that extends in a circumferential direction and is disposed between the inflow end and the outflow end, and
  the distal row of cells is positioned on a distal side of the groove so as to be closer to the outflow end than the groove.

9. The replacement heart valve system according to claim 7, wherein the arm extends from an apex of a cell of the distal row.

10. The replacement heart valve system according to claim 1, wherein the proximal-most cells of the first row further include a pair of joined cells directly joined with each other.

11. The replacement heart valve system according to claim 1, wherein the proximal-most cells of the first row include pairs of joined cells directly joined with each other, the pairs being disposed at equal distances from one another around a circumference of the inflow end of the tubular body.

12. The replacement heart valve system according to claim 1, wherein the tubular body further comprises a groove that extends in a circumferential direction and is disposed between the inflow end and the outflow end.

13. The replacement heart valve system according to claim 12, wherein the outer diameter of the inflow end increases along a direction from the groove to the proximal-most portion.

14. The replacement heart valve system according to claim 1, wherein the first row includes fewer cells than a remainder of circumferential rows of the tubular body.

15. The replacement heart valve system according to claim 1, wherein the space has a circumferential dimension substantially equal to a circumferential dimension of a proximal-most cell.

16. The replacement heart valve system according to claim 1, wherein at least one of the circumferentially adjacent cells that are spaced from each other includes a seal, and the seal extends in a circumferential direction from a strut forming a side of one of the circumferentially adjacent cells that defines a side of the space.

* * * * *